United States Patent [19]

Ashe et al.

[11] 3,967,122

[45] June 29, 1976

[54] RADIATION ANALYZER UTILIZING SELECTIVE ATTENUATION

[75] Inventors: John B. Ashe; Peter F. Berry; James D. Hall, all of Austin, Tex.

[73] Assignee: G. D. Searle & Co., Skokie, Ill.

[22] Filed: Dec. 5, 1974

[21] Appl. No.: 529,857

Related U.S. Application Data

[62] Division of Ser. No. 366,488, June 4, 1973, Pat. No. 3,859,525.

[52] U.S. Cl. ............................ 250/367; 250/368
[51] Int. Cl.² ........................................ G01T 1/20
[58] Field of Search ............ 250/361, 363, 367, 368

[56] References Cited
UNITED STATES PATENTS

| | | | |
|---|---|---|---|
| 3,413,466 | 11/1968 | Allen, Jr. .................... | 250/367 X |
| 3,665,191 | 5/1972 | Moody ......................... | 250/368 |
| 3,714,431 | 1/1973 | Sterk ........................... | 250/367 |

Primary Examiner—Archie R. Borchelt
Attorney, Agent, or Firm—Walter C. Ramm; Peter J. Sgarbossa; Helmuth A. Wegner

[57] ABSTRACT

A radiation analyzer which employs a single photodetector and a plurality of scintillators. Light filters interposed between selected ones of the scintillators selectively attenuate radiation of a predetermined energy range. Plural analyzers each associated with a single scintillator and each receiving electrical pulses from the photodetector attenuated to a different degree are adjusted to tabulate pulses of amplitudes which differ in accordance with the degree of attenuation of pulses received by the analyzers from the photodetector.

3 Claims, 6 Drawing Figures

RADIATION ANALYZER UTILIZING SELECTIVE ATTENUATION

This is a division of application Ser. No. 366,488, filed June 4, 1973, now U.S. Pat. No. 3,859,525.

The present invention relates to a radiation analyzer which processes radiation signals from a plurality of scintillators to permit identification of the individual radiation events with one of the scintillators after amplification by a common photodetector.

BACKGROUND OF THE INVENTION

In many existing non-dispersive fluorescent x-ray analyzers, sequential comparative radiation measurements are necessary, perhaps with "balanced filters" to achieve adequate energy resolution. In the comparative measurement technique, substances of known and unknown compositions are irradiated. Fluorescent x-ray radiation emanating therefrom is measured in sequential operations of the radiation analyzer, so that the measurement results of the substance of unknown composition can be determined with respect to the measurement results of the substance of known composition. However, variations in measuring technique, instrument gain, and voltage fluctuations significantly affect the results obtained.

Balanced filters together transmit a narrow band of x-ray energies such that transmission by each filter of a filter pair outside of this band is "balanced," but transmission within the band is significantly different. The difference in the signal transmitted through the filters is proportional to the incident radiation intensity in the narrow band of unbalance. This narrow band of unbalance can be chosen to include the characteristic fluorescent radiation energy for an element of interest, and is typically less than 5 KeV in width. The balanced filter technique permits x-ray intensity measurements to be made with substantially higher energy resolution than the inherent resolution of the detector. The energy resolution is governed by the pass band of the filter pair rather than the inherent properties of the detector.

Stated another way, the term balanced filters, as used herein, refers to a pair of filters having different transmission properties in a narrow energy band of interest but having transmission properties closely matched for all other energies of interest. The quantitative determination of the amount of an element of interest is determined by the difference of the transmitted signals passed by the filters. One filter, hereinafter termed the "transmitting" filter, passes a greater portion of the radiation in a narrow energy range of interest than does the other filter, hereinafter termed the "absorbing" filter.

Several types of balanced filter analyzers are currently in use. One type sequentially interposes each of a pair of filters between the substance to be analyzed and a scintillator during a measuring cycle. A radiation count is taken for a predetermined time with one of the filters interposed between the detector and the specimen to be analyzed. The count is recorded and the other filter is placed in position, with radiation counts then being recorded for an equal time interval. The background radiation is nominally equivalent in both of the measuring intervals, but the extent by which the radiation count with the transmitting filter exceeds the radiation count with the absorbing filter is indicative of the extent to which the element of interest is present.

In other types of balanced filter analyzers, dual radiation detectors or dissimilar scintillators are utilized, one with the transmitting filter and the other with the absorbing filter. The counts from the two detectors are compared to determine the amount of radiation attributable to the elements of interest. In the known dissimilar scintillator system the respective signals are separated by rise time techniques. This differential count is indicative of the quantity of the element which is present, as previously discussed.

A treatment of balanced filters generally may be found in the book "X-Ray Analysis Papers", edited by William Parish, Centrex Publishing Company, Eindoven, 1965, at pages 36 and 37.

SUMMARY OF THE INVENTION

It is an object of the present invention to provide radiation detection apparatus utilizing a single photodetector to obtain a measurement proportional to the quantity of an element of interest which is present. Operation of the apparatus is performed in a single measurement cycle.

It is a further object of the present invention to achieve measurement in a single cycle, or counting step, using a single photodetector in order to eliminate the possibility of error due to movement of the detector or specimen between counting periods or due to internal electrical variations within the instrument or due to unpredicted fluctuations in background radiation during different measurement intervals.

It is an object to achieve the foregoing advantages without resorting to use of more than one photodetector. This eliminates the necessity for synchronizing photodetector gain and obviates the introduction of error caused by differing photodetector response characteristics. The present invention also reduces the expense required to manufacture a radiation detection apparatus by obviating the necessity for a second photodetector.

It is a further object of this invention to provide a system for simultaneously quantifying radiation signals from a plurality of independent scintillators with a single photodetector.

In addition the radiation detection apparatus of this invention can be used to replace a conventional detector system used to concurrently count radioactive events in a plurality of samples. For example, the radiation detection apparatus of this invention, using a single photodetector, can be used to replace the crystals and photodetectors in a radiation detecting device such as that illustrated in U.S. Pat. application Ser. No. 237,662, filed on Mar. 24, 1972 now U.S. Pat. No. 3,796,879.

In a broad aspect this invention is, in a radiation detection apparatus utilizing a plurality of scintillators, the improvement comprising a single photodetector for generating electrical pulses in optical communication with the scintillators, a light filter for attenuating incident light energy by at least 10 percent positioned between the photodetector and at least one and less than all of said scintillators, a first signal analyzer connected to said photodetector for accepting electrical pulses in a predetermined amplitude range, and a second signal analyzer connected to said photodetector and set to accept electrical pulses having amplitudes falling within the aforesaid predetermined energy range but diminished by the amount by which the aforesaid light filter attenuates incident light energy.

While the terms "filter" and "scintillator" may be used in the singular, they should also be taken to include those situations where one filter or scintillator may be comprised of several identical component elements.

In one embodiment of the invention, a pair of balanced radiation filters are employed in addition to a light filter. Each filter in the balanced filter pair absorbs radiation to the same extent outside of a narrow radiation energy range of interest. An imbalance between the filters of a balanced filter pair implies differing absorption in the narrow energy range of interest. The difference in the signals passed by the filters in the balanced filter pair is proportional to the imbalance of the radiation intensity in the narrow energy range of interest.

While attenuation of at least 10 percent has been specified as being desirable, the minimum acceptable degree of attenuation may be more or even less, depending upon the response function of the radiation detectors involved. The most important factor is that there must be significant resolution between the pulse spectra generated from each of the scintillation detectors.

BRIEF DESCRIPTION OF THE INVENTION

The invention may be more fully explained and completely understood by reference to the accompanying drawings in which:

FIG. 1 is a schematic representation of one embodiment of this invention,

FIG. 2 is an enlarged cross sectional elevational view of the radiation processing assembly taken along the lines 2—2 of FIG. 3, FIG. 3 is an enlarged plan view of a radiation processing assembly taken along the lines 3—3 of FIG. 2, FIG. 4 graphically depicts the pulse height spectra recorded using the apparatus of this invention, FIG. 5 illustrates in partial section a portion of the apparatus of one embodiment of this invention, and FIG. 6 depicts schematically a portion of an alternative embodiment of this invention.

DETAILED DESCRIPTION OF THE INVENTION

Figure 1:
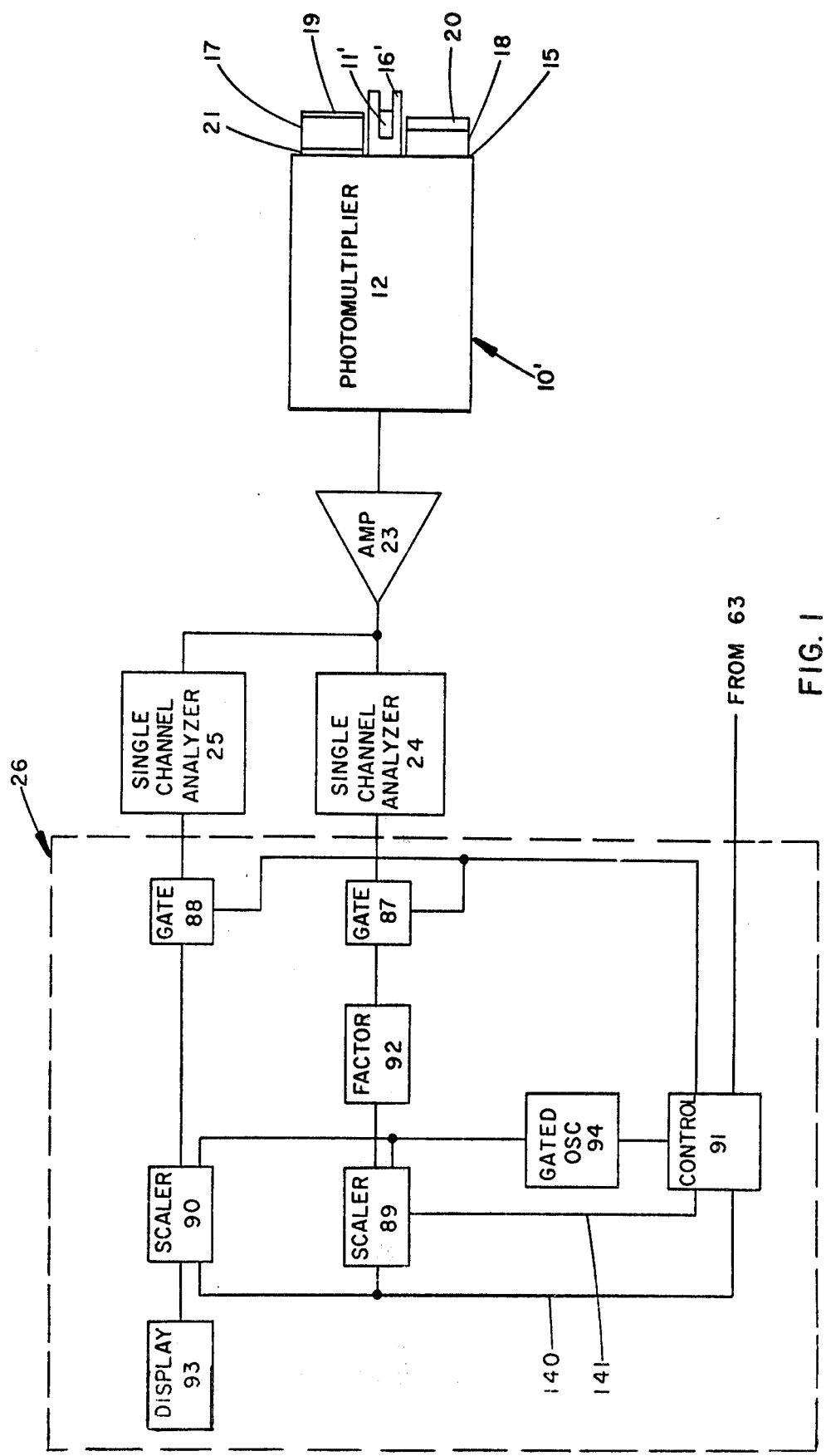

Referring now to FIG. 1, there is illustrated a fluorescent radiation detection apparatus 10' employing a primary radiation source 11'. A single photomultiplier or photodetector 12 is utilized having a photosensitive surface 15. Detecting elements in the form of distinct scintillator means 17 and 18 are optically shielded from each other and are in optical communication with the photosensitive face 15. A shield 16' is provided to shield detecting elements 17 and 18 from primary radiation source 11'. One radiation filter 19 of a balanced filter pair is located proximate to the scintillator 17. Radiation absorbing filter 19 strongly absorbs fluorescent radiation of the element of interest. Radiation transmitting filter 20 is located proximate to the scintillator 18. Filter 20 has energy response attenuation characteristics similar to those of filter 19 at energy levels other than in a predetermined narrow energy range which is characteristic of the element of interest. Filter 20 only weakly absorbs radiation in this predetermined narrow energy range. While the scintillators 17 and 18 are both in optical communication with photosensitive face 15, a light filter 21 for uniformly attenuating incident light energy typically by at least 10 percent is positioned between the photosensitive surface 15 and the scintillator 17. Alternatively, the light filter 21 could be interposed between the photosensitive surface 15 and scintillator 18. It is only imperative that this light filter be used with either the scintillator 17 associated with filter 19 or the scintillator 18 associated with filter 20, but not with both.

Figure 4:
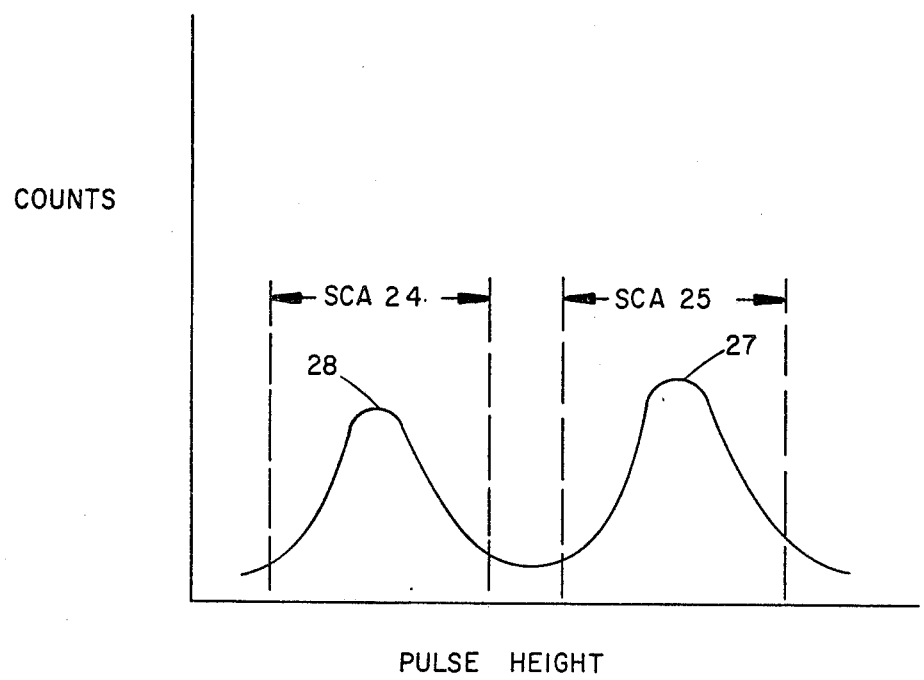

The photomultiplier 12 is connected to an amplifier 23 and then in parallel to separate single channel analyzers 24 and 25. The electrical pulse energy window of the single channel analyzer 24 is indicated as SCA 24 in FIG. 4. Similarly, the electrical pulse energy window of single channel analyzer 25 is indicated as SCA 25 in FIG. 4. By reference to FIG. 4 it can be seen that the energy window of analyzer 24 is significantly less than the energy window of analyzer 25, and there is substantial resolution between the pulse spectra 28 and 27 from the scintillators 17 and 18 respectively. Since the light filter 21 is interposed between the photosensitive surface 15 and the scintillator 17, the spectrum 28 of scintillations from the scintillator 17 is at a much lower level than the spectrum of scintillations from scintillator 18. The average pulse energy under curve 28 is about 30% of the average pulse energy under curve 27 if filter 21 attenuates scintillations from scintillator 17 by about 70%, as in the illustrated embodiment. The area under the curve 28 would be identical to the area under the curve 27 if the balanced radiation filters 19 and 20 were not present. Since the filters 19 and 20 are positioned as indicated, however, there is a difference in the two areas. This difference is proportional to the amount of the fluorescent radiation excited by source 11' in the element of interest. The count differential between the spectrum 27 and the spectrum 28 is therefore proportional to the amount of an element of interest which is present in the specimen under study.

The outputs of single channel analyzers 24 and 25 are connected to a counting means indicated generally as 26. In the embodiment of FIG. 1, the outputs of single channel analyzers 24 and 25 are gated respectively by gates 87 and 88 into separate scalers 89 and 90 for a preselected time interval as determined by the program control unit 91. The output from single channel analyzer 24 passes through a factor gate 92 that allows only a fraction of the pulses from single channel analyzer 24 to pass through to scaler 89. This fraction is usually from between about 0.8 and about 1.0 and compensates for a slight built-in imbalance in the filters. Together with the selected time interval, this facilitates direct readout from the display unit 93 in milligrams per square centimeter of the element of interest in the specimen under study. At the end of the predetermined time interval, the program control unit 91 turns on a gated oscillator 94 which counts the same number of pulses into each of the scalers 89 and 90 until scaler 89 overflows. The overflow pulse causes the program control 91 to cut off the gated oscillator 94. At this time, scaler 90 will contain the difference between the two timed counts into scalers 89 and 90. Since the timed count into scaler 90 will always be greater than the timed counts into scaler 89 (except for statistical deviations), the count in scaler 90 represents the concentration of the element of interest in the specimen analyzed, and this concentration is read directly from display unit 93. Because of statistical deviations, scaler 90 will occasionally have fewer counts recorded than are recorded in scaler 89 prior to actuation of the gated oscillator 94. For this reason, an overflow signal from both scalers 89 and 90 is required on circuits 140 and 141 for a zero reading to be displayed in the unit 93.

Figure 3:
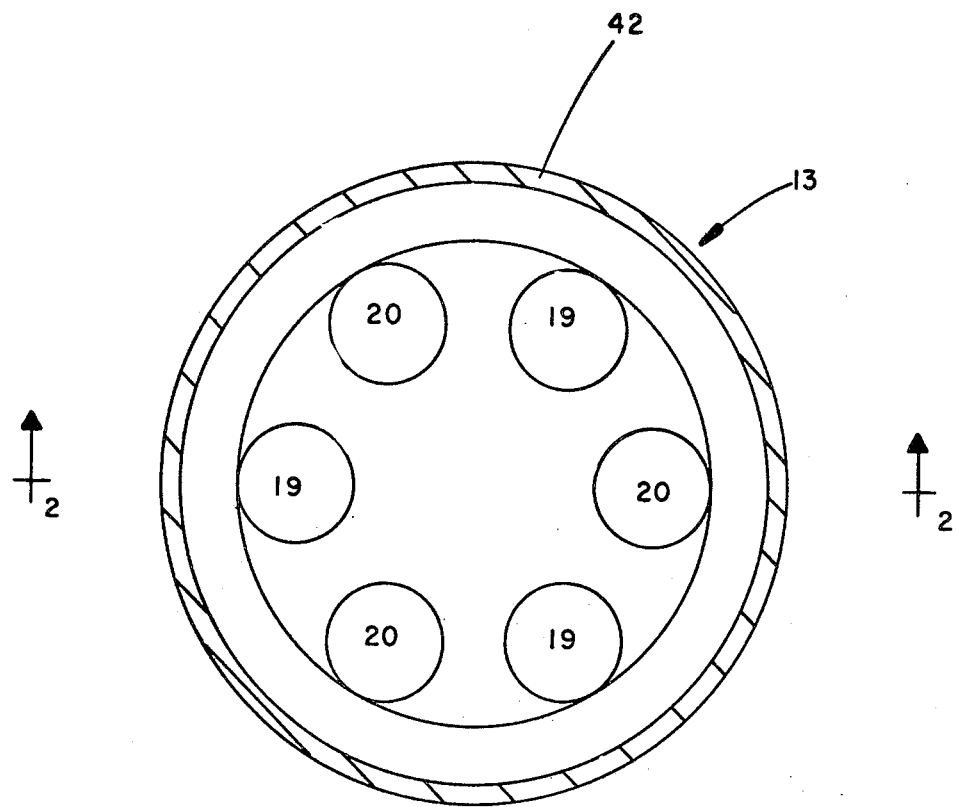
Figure 2:
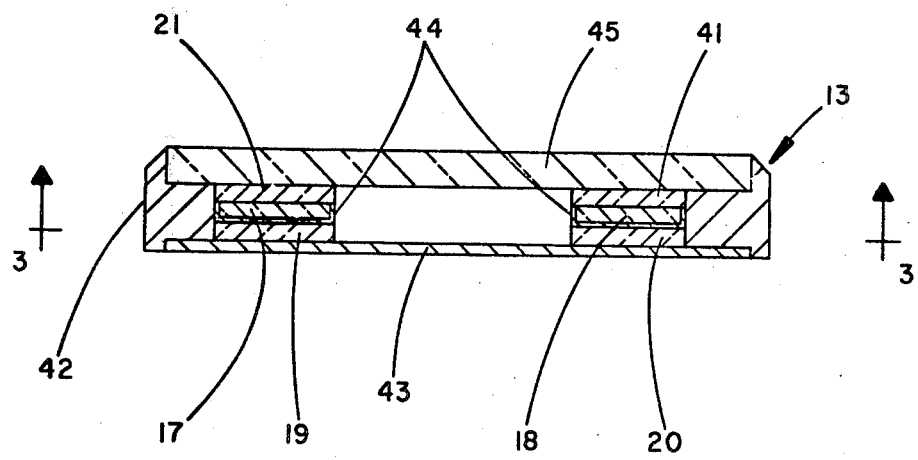

The operation of this embodiment of the apparatus of this invention may be further explained by reference to FIGS. 2, 3 and 5 of the drawings, in which the elements marked with unprimed designation correspond to their primed counterpart elements of FIG. 1. It can be seen that in a practical embodiment, rather than using single element filters, the filters 19 and 20 are typically comprised of a number of identical elements employed in a configuration as illustrated in FIG. 3. Th scintillators 17 and 18 (in FIG. 2), as well as their respectively corresponding radiation filters 19 and 20, are encapsulated in a radiation processing capsule 13. This radiation processing capsule is comprised of a fluorescent radiation entrance window 43 laterally retained by radiation processor housing 42. The radiation filters 19 and 20 are positioned against the interior surface of the entrance window 43 and scintillators 17 and 18, partially enclosed by the reflectors 44, are respectively aligned therewith. The elements of the light filter 21 are aligned with the elements of scintillators 17 and radiation absorbing filters 19. The elements of light filter 21 uniformly attenuate scintillations produced in the scintillator 17 and transmit only about 30 percent of the light generated therein, although a light transmission factor of as much as about 90 percent is acceptable. To provide consistency of geometry, light filter blanks 41 are aligned with scintillators 18 and radiation transmitting filters 20. The filter blanks 41 do not attenuate to any appreciable degree the scintillations emanating from the scintillators 18, however, and the light transmission factor of the light filter blanks 41 is as large as possible and approaches 100 percent. A light pipe or window 45 completes the structure of the radiation processing capsule 13.

Figure 5:
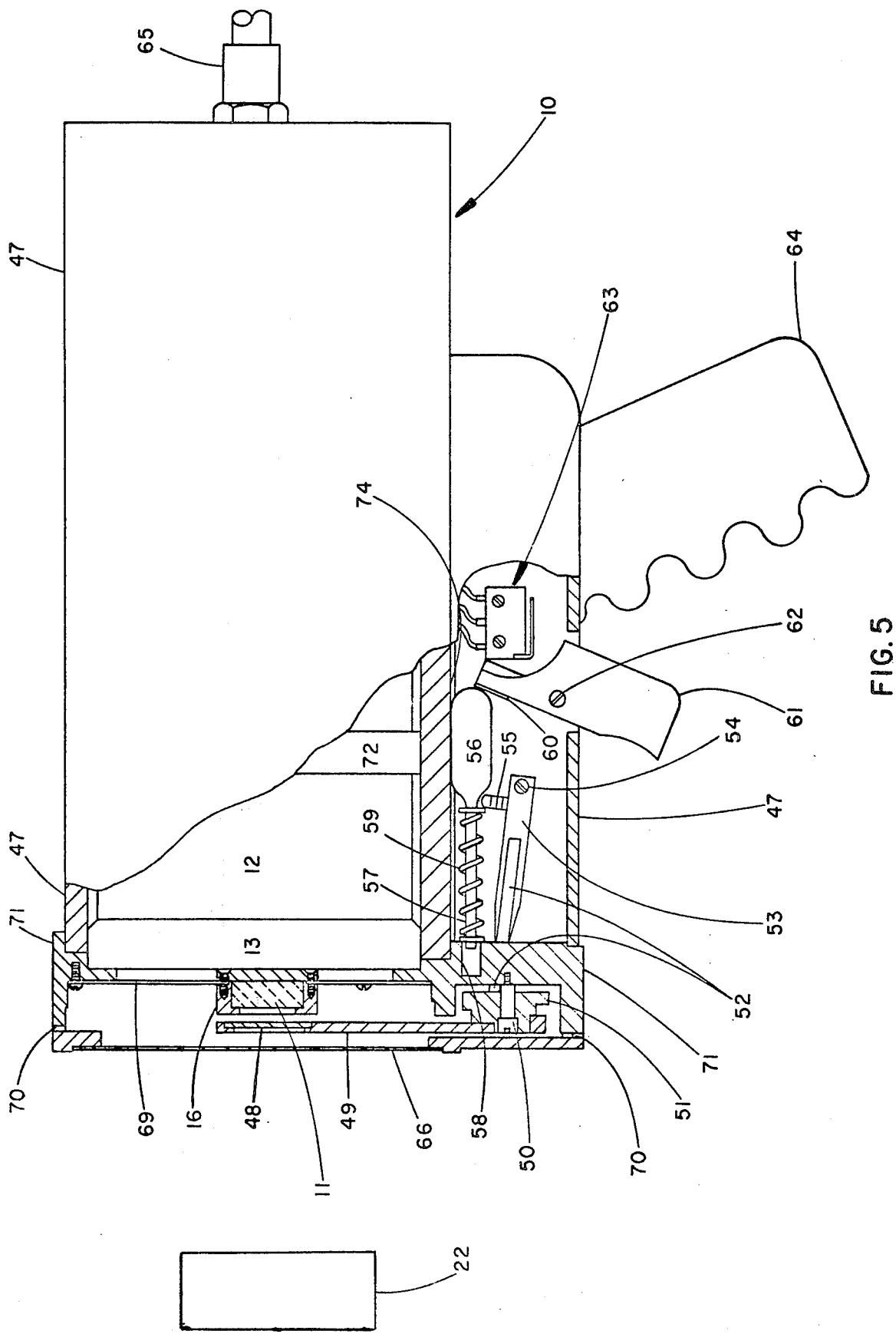

To quantitatively detect the presence of the element of interest in a specimen, such as a specimen 22 in FIG. 5, the specimen is subjected to a primary source of radiation to produce fluorescent radiation therein. One particularly useful application is the determination of the lead content of paint. In this instance, a specimen of paint is exposed to radiation from a primary radiation source 11. Typically, a radiation source 11 is comprised of x-ray sources such as cobalt-57. A paint sample is exposed to the cobalt-57 radiation by grasping the handle 64 of the fluorescent radiation detection apparatus 10 illustrated in FIG. 5, and depressing the trigger 61. Trigger 61 rotates about an axis 62 so that the pad 60 forces cam 56 forward in opposition to the bias of the compression spring 59. The upper surface of cam 56 rides in a longitudinal groove 74 in radiation probe housing 47. Cam 56 is also guided in its longitudinal motion by pin 57 which moves within the guide cavity 58 in the end enclosure 71 of the radiation probe 10.

As cam 56 moves forward, its lower surface forces the adjustable cam follower 55 downward, thereby causing an actuator arm 53 to rotate in a counterclockwise direction about the pivot pin 54. A spline 52, attached to actuator arm 53, rides in a vertical track (not shown) in end enclosure 71, and passes between two adjacent teeth of the spur gear 51. As spline 52 and actuator arm 53 are rotated counterclockwise in FIG. 5, spur gear 51 is also turned about its axis 50, carrying with it the shutter arm 49 and source shield 48. Shutter arm 49 and source shield 48 rotate perpendicular to the plane of FIG. 5 thereby allowing a primary radiation source 11 to emit x-rays that pass through the plastic window 66 to irradiate the specimen. The primary radiation source 11 is shielded from radiation processing capsule 13 and is held in place at the geometric center of radiation processing unit 13 by support 69 which is fastened to end closure 71.

As trigger 61 is depressed, it actuates a microswitch 63 which sends signals to the program control unit 91 of FIG. 1 by way of an electrical interlock 65.

As the specimen is irradiated, it emits fluorescent radiation, a fraction of which, along with scattered radiation, returns to the radiation probe and passes through the window 66 and support 69 to strike the radiation processing unit 13. Thereon it exposes simultaneously the radiation absorbing filter 19, which may be considered to be the first filter means, and the radiation transmitting filter 20, which may be considered as the second filter means. For application to the measurement of the lead content of paint, the first filter is typically comprised of rhenium metal, while the second filter is typically comprised of iridium metal. These particular metals are used because they have very similar attenuation characteristics for radiation over a wide range of energies with the notable exception of the narrow energy range from about 73 to about 75 keV. In the energy band from 73 to 75 keV the iridium filter 20 transmits radiation to a much greater degree than does the rhenium filter 19. This narrow energy range embraces the dominant K x-ray emanations of lead. It would also be possible to use other materials; for example, tungsten and platinum or tantalum and gold, for the filters 19 and 20.

The radiation transmitted through the filters 19 and 20 is passed separately to a distinct scintillating medium associated therewith to produce corresponding light scintillations from scintillators 17 and 18. The light scintillations are processed by attenuating by at least about 10 percent, and preferably by at least 50 percent, the intensity of scintillations occurring in the scintillating mediums associated with either the radiation absorbing filters 19 or the radiation transmitting filters 20, but not both. From the radiation processing unit 13, light from the scintillators is passed to the photosensitive surface of the photodetector 12. Photodetector 12 generates electrical pulses having amplitudes proportional to the intensity of scintillations received. These electrical pulses are amplified and discrimination is carried out among the electrical pulses by accepting pulses in a pulse amplitude range such as SCA 25, which pulse amplitude range includes a great percentage of pulses characteristic of the element of interest as well as other pulse energies. That is, in the case of determining the lead content in a specimen, the pulse amplitude range of SCA 25 will include, but is not limited to, pulses from the energy band between 73 and 75 keV. While there is only a single radiation energy range of acceptance, the use of light filter 21 makes two electrical pulse amplitude ranges necessary. The first electrical pulse amplitude range is indicated as SCA 25 in FIG. 4, while a second pulse amplitude range is indicated as SCA 24. The upper and lower electrical pulse limits of SCA 24 are equal in energy to the pulses of the first pulse amplitude range diminished by the amount by which light filter 21 attenuates incident light energy. That is, if light emanating from light filter 21 has an intensity of only 30 percent, of the intensity of light incident upon light filter 21, the upper and lower discriminators for SCA 24 should be 30 percent respectively of the upper and lower discriminators for SCA 25. The number of electrical pulses in the electrical pulse amplitude range SCA 25, and the product of subtraction is then compared with a corresponding number associated with a known amount of the element of interest in order to determine the extent to which the element of interest is present in the specimen 22. In other words, the number recorded in the counter 26 is compared with a number previously recorded in examining a specimen containing a known amount of lead. The ratio between these numbers obtained from counter 26 is indicative of the amount of lead present in the specimen 22.

Figure 6:
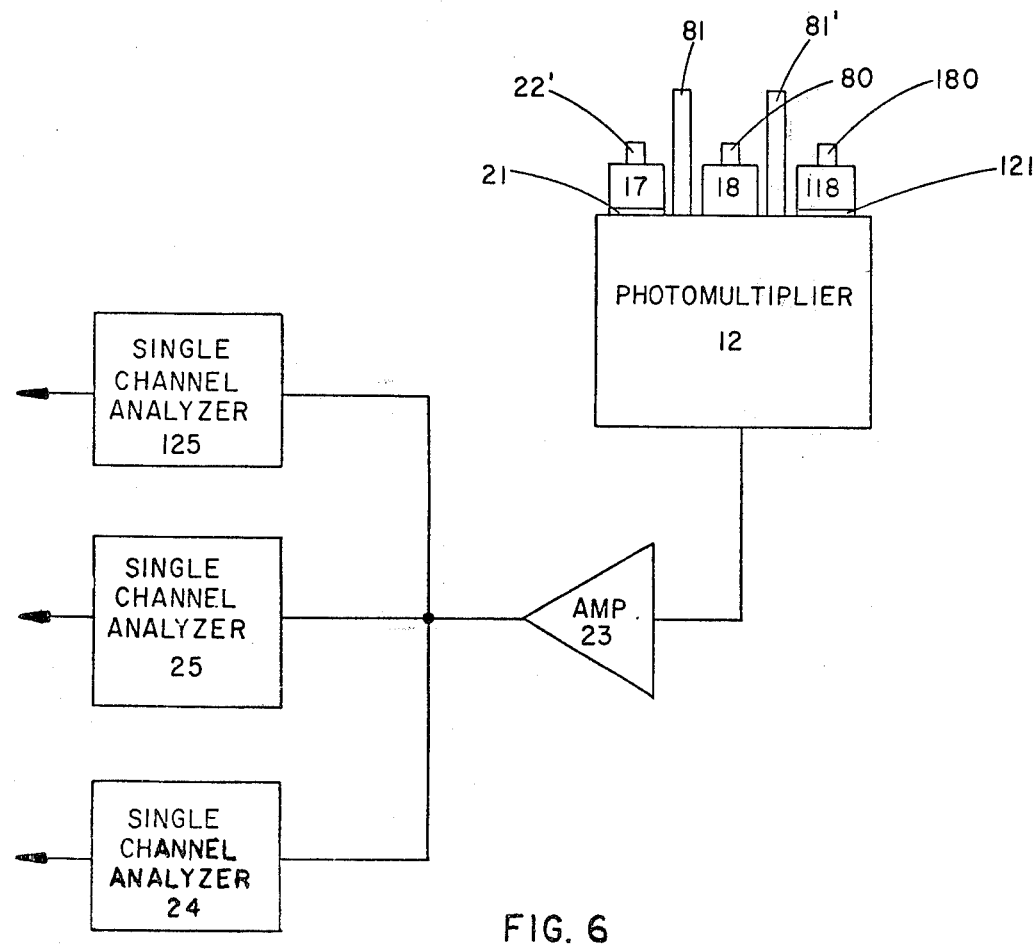

As alternative embodiment of a radiation detection apparatus of this invention is illustrated in FIG. 6. The embodiment differs from that of FIG. 1 in several ways. Three scintillators, 17, 18 and 118, are used along with two classes of light filters 21 and 121. As in other embodiments, and as depicted in FIG. 3, a class will include a plurality of filter elements where a plurality of scintillator elements are used. Each of the filter elements within a class of filters is positioned between the photodetector 12 and a single scintillator, as illustrated. The attenuation of each class of light filters differs from that of any other class by at least 10 percent. Therefore, if filter 121 attenuates light to the greatest degree, the light reaching photodetector 12 from scintillator 17 will be attenuated by at least 10 percent when compared with the light from scintillator 18, while the light from scintillator 118 will be attenuated by at least 20 percent and by at least 10% more than attenuation of light from scintillator 17. For example, filter 21 may attenuate light by 40% while filter 121 attenuates light by 70 percent. In a corresponding fashion, the signal analyzers 24, 25 and 125 are adjusted to accept electrical pulses in separate predetermined amplitude ranges. Signal analyzer 25 is adjusted to accept electrical pulses in an energy range within which unattenuated electrical pulses fall. Signal analyzers 24 and 125 are adjusted to accept electrical pulses having amplitudes corresponding to the energy range SCA 25, but diminished to the extent that the associated light filter attenuates incident light energy. That is, the acceptable range of channel analyzer 125 will be lower than the acceptable range of channel analyzer 24 to the extent that the attenuation of filter 121 exceeds the attenuation of filter 21. Continuing the example, the acceptable range of channel analyzer 125 will be 30 percent of the acceptable range of channel analyzer 25, while the acceptable range of channel analyzer 24 will be 60 percent of the acceptable range of channel analyzer 25.

An additional difference from the device of FIG. 1 is that balanced radiation filters are not employed. To utilize the device, radiation source 80 of known radiation characteristics may be positioned proximate to only the scintillator 18. Lead radiation shields 81 and 81' are interposed between the known radiation source 80 and scintillators 17 and 118 so that radiation from substances 22 and 180 to be analyzed do not produce scintillations in scintillator 18 and so that radiation source 80 does not produce scintillations in scintillators 17 and 118. In this way, the pulses counted in window SCA 24 and in the pulse amplitude window of channel analyzer 125 may be compared against pulses from the known source counted in window SCA 25 so that a plurality of specimens may be concurrently compared against a uniform reference, such as radiation source 80. Alternatively, of course, the radiation source 80 could be located near either the scintillator 17 or the scintillator 118 and shielded from the other scintillators. It is only important that source 80 not cause scintillations in more than one of the scintillators and that radiations from substances 22' and 180 produce scintillations only in their associated scintillator.

In an alternative use of the device of FIG. 6, three unknown radiation sources may be concurrently analyzed and compared against known standards. Each unknown radiation source is positioned proximate to a separate one of the scintillators as illustrated. The lead shields 81 act to shield each scintillator from radiation emanating from each of the radiation sources positioned proximate thereto. An optical shield about each scintillator is also used to isolate each scintillator from the other scintillators. As before, scintillations reaching the photodetector are selectively optically attenuated. The degree of attenuation of scintillations from each of the scintillators 17, 18 and 118 differs from the degree of attenuation of light from any other scintillator by at least 20 percent. The pulses falling within the amplitude windows of signal analyzers 24, 25 and 125 may then be identified as to the scintillator causing the pulse. That is, scintillations having an amplitude of interest occurring in scintillator 18 will cause a pulse to emanate from channel analyzer 25, while scintillations occurring in scintillators 17 and 118 will respectively cause pulses to emanate from channel analyzers 24 and 125. In this manner, a single photodetector 12 may be used for the concurrent analysis of radioactive sources in radiation measuring devices.

The foregoing illustrative examples and drawings are provided for purposes of explanation only, and no limitation should be construed therefrom beyond those requirements defined by the claims of this invention.

We claim as our invention:

1. In a radiation detection apparatus utilizing a plurality of scintillators, the improvement comprising the arrangement of said scintillators in a radiation detection plane, a single photodetector for generating electrical pulses and having a photosensitive surface parallel to said radiation detection plane in optical communication with the scintillators, a light filter for uniformly attenuating incident light energy by at least 10 percent positioned between the photodetector and at least one and less than all of said scintillators, a first signal analyzer connected to said photodetector for accepting electrical pulses in a predetermined amplitude range generated by radioactive events occurring proximate to said radiation detection plane, and a second signal analyzer connected to said photodetector and set to accept contemporaneous electrical pulses having amplitudes falling with the aforesaid predetermined energy range but diminished by the amount by which the aforesaid light filter attenuates incident light energy and likewise generated by radioactive events occurring proximate to said radiation detection plane.

2. In a radiation detection apparatus utilizing at least three scintillators having at least one element each, the improvement comprising, the arrangement of all of said scintillators in a radiation detection plane a single photodetector for generating electrical pulses and having a single photosensitive surface parallel to and in optical communication with said scintillators, at least two classes of light filters, each class of filters being positioned between the photodetector and all of the elements of a single scintillator and uniformly attenuating incident light energy within a class by at least 10 percent, and wherein the attenuation of each class of light filters differs from the attenuation of any other class by at least 10 percent, and at least three signal analyzers, each associated with one of the aforesaid scintillators, are connected to said photodetector for accepting electrical pulses in separate predetermined amplitude ranges, a first of the signal analyzers being adjusted to accept electrical pulses in an energy range produced by scintillations from a first one of the scintillators in response to radiation penetrating said radiation detection plane at a particular time, while others of the signal analyzers are adjusted to contemporaneously accept electrical pulses having amplitudes corresponding to the energy range of the first signal analyzer, in response to radiation likewise penetrating said radiation detection plane at the same aforesaid time but modified to the extent that the associated light filter attenuates incident light energy by an amount different than the amount which any light filter attenuates light energy from said first scintillator.

3. A radiation apparatus comprising:
  a. a single phtodetector having a planar photosensitive surface,
  b. at least three distinct scintillator means optically shielded from each other and located in a radiation detection plane parallel to and in optical communication with said photosensitive face,
  c. at least two classes of light filters for attenuating incident light energy uniformly within a class and by an amount of at least 10% and wherein the degree of attenuation of each class differs from that of any other class by at least 10%, all of the filters of a class being positioned between said photosensitive face and a single one of the three scintillator means,
  d. at least three separate channel analyzers connected in parallel to said photodetector wherein the electrical pulse energy window of a first one of said channel analyzers is set to accept those electrical pulses in an energy range produced by scintillations from a first one of the scintillator means, while other of the signal analyzers are adjusted to accept electrical pulses having amplitudes corresponding to the energy window of the first of said channel analyzers but modified by the amount by which the associated light filter attenuates incident light energy from the associated scintillator means by an amount different than the amount which any light filter attenuates light energy from said first scintillator means, and
  e. counting means connected to said channel analyzers for tabulating contemporaneous electrical pulses from each of said channel analyzers in response to conditions of radiation at said radiation detection plane at any particular time.

* * * * *